(12) United States Patent
Casey et al.

(10) Patent No.: US 7,834,224 B1
(45) Date of Patent: Nov. 16, 2010

(54) LIGAND IRON CATALYSTS FOR SELECTIVE HYDROGENATION

(75) Inventors: Charles P. Casey, Madison, WI (US); Hairong Guan, Cincinnati, OH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 617 days.

(21) Appl. No.: 11/942,774

(22) Filed: Nov. 20, 2007

(51) Int. Cl.
*C07C 27/04* (2006.01)
*C07C 29/14* (2006.01)
*C07C 209/00* (2006.01)
*C07F 15/00* (2006.01)

(52) U.S. Cl. ................. 568/885; 568/881; 564/489; 556/141; 502/152

(58) Field of Classification Search ................. 502/152; 556/141; 564/489; 568/881, 885
See application file for complete search history.

(56) References Cited

OTHER PUBLICATIONS

J. Peters et al., X-ray Crystal Structure Of The Fe-Only Hydrogenase (Cpl) From Clostridium pasteurian To 1.8 Angstrom Resolution, 282 1853 et seq. (1998).

Y. Nicolet et al., Desulfovibrio Desulfuricans Iron Hydrogenase: The Structure Shows Unusual Coordination To An Active Site Fe Binuclear Center, 7 Structure 13-23 (1999).

H.-J. Fan et al., A Capable Bridging Ligand for Fe-Only Hydrogenase . . . , 123 J. Am. Chem. Soc. 3828-3829 (2001).

R. Noyori et al., Asymmetric Catalysis By Architectural and Functional Molecular Engineering . . . , 40 Angew. Chem. Int. Ed. 40-73 (2001).

T. Ikariya et al., Bifunctional Transition Melta-Based Molecular Catalysts For Asymmetric Syntheses, 4 Org. Biomol. Chem. 393-406 (2006).

Y. Shvo et al., A New Group Of Ruthenium Complexes: Structure And Catalysis, 108 J. Am. Chem. Soc. 7400-7402 (1986).

C. Casey et al., Hydrogen Transfer To Carbonyls And Imines . . . , 123 J. Am. Chem. Soc. 1090-1100 (2001).

J. Casey et al.,Isomerization And Deuterium Scrambling Evidence For A Change . . . , 127 J. Am. Chem. Soc. 1883-1894 (2005).

J. Casey et al., Reduction Of Imines By Hydroxycyclopentadienyl Ruthenium Hydride . . . , 127 J. Am. Chem. Soc. 14062-14071 (2005).

J. Casey et al., Stereochemistry Of Imine Reduction By A Hydroxycyclopentadienyl Ruthenium Hydride, 128 J. Am. Chem. Soc. 2286-2293 (2006).

See M. Schroeder et al., Pentacarbonyliron(O) Photocatalyzed Hydrogenation And Isomerization Of Olefins, 98 J. Am. Chem. Soc. 551-558 (1976).

S. Bart et al., Preparation And Molecular And Electronic Structures of Iron(O) Dinitrogen . . . , 126 J. Am. Chem. Soc. 13794-13807 (2004).

E. Daida et al., Considering FeII/IV Redox Processes As Mechanistically Relevant . . . , 43 J. C. Inorg. Chem. 7474-7485 (2004).

M. Radhi et al., Hydrogenation Of N-Benzylideneaniline With Molecular Hydrogen Using Iron Pentacarbonyl As Catalyst Precursor, 262 J. Organomet. Chem. 359-364 (1984).

(Continued)

*Primary Examiner*—Porfirio Nazario Gonzalez
(74) *Attorney, Agent, or Firm*—Quarles & Brady LLP (57) ABSTRACT

Disclosed are iron ligand catalysts for selective hydrogenation of aldehydes, ketones and imines. A catalyst such as dicarbonyl iron hydride hydroxycyclopentadiene) complex uses the OH on the five member ring and hydrogen linked to the iron to facilitate hydrogenation reactions, particularly in the presence of hydrogen gas.

18 Claims, 4 Drawing Sheets

OTHER PUBLICATIONS

H.-J. Knoelker et al., Demetalation Of Tricarbonyl(cyclopentadieone)iron Complexes . . . , 38 Angew. Chem. Int. Ed. 2064-2066 (1999).

C. Casey et al., Unexpected Formation Of The Isopropylamine Complex . . . , 21 Organometallics 1955-1959 (2002).

C. Casey et al., An Efficient And Chemoselective Iron Catalyst For The Hydrogenation Of Ketones, 5816-5817 (Apr. 17, 2007) (not prior art).

R. Bullock, An Iron Catalyst For Ketone Hydrogenations Under Mild Conditions, 2007 Angew. Chem. 03053 (9 pages) (2007) (not prior art).

Steven W. Singer, on pp. 232-239 of an appendix of his PhD thesis entitled "Formation And Reactions Of A Hydroxycyclopentadienyl Ruthenium Hydride: An Organometallic Complex Containing Electronically Coupled Acidic And Hydridic Hydrogens", University Of Wisconsin (2002).

| entry | substrate | product | time | yield |
|---|---|---|---|---|
| 1 | PhCHO | PhCH₂OH | 1 h | 90% (100%) |
| 2 | PhCH₂CH₂COCH₃ | PhCH₂CH₂CH(OH)CH₃ | 24 h | 88% (98%) |
| 3 | X = H | | 20 h | 83% (99%) |
| 4 | X = Br | | 24 h | 91% (99%) |
| 5 | X = I | | 20 h | 84% (99%) |
| 6 | X = NO₂ | | 6 h | 89% (99%) |
| 7 | X = CN | | 19 h | (< 1%) |
| 8 | PhCOPh | PhCH(OH)Ph | 72 h | 55% (69%) |
| 9 | PhCOCF₃ | PhCH(OH)CF₃ | 10 min | 91% (100%) |
| 10 | PhCOCOPh | PhCH(OH)CH(OH)Ph | 2 h | 86% (100%) (meso/dl = 25) |
| 11 | (hex-5-en-2-one) | (hex-5-en-2-ol) | 36 h | 87% (100%) |
| 12 | R = H | | 24 h | 57% (71%) |
| 13 | R = CH₂Ph | | 20 h | 84% (87%) |
| 14 | PhCO-cyclopropyl | PhCH(OH)-cyclopropyl | 68 h | 46% (50%) |
| 15 | 2-acetylpyridine | 1-(pyridin-2-yl)ethanol | 8 h | 87% (100%) |
| 16 | PhCH=NPh | PhCH₂NHPh | 40 h | 50% (54%) |

LIGAND IRON CATALYSTS FOR SELECTIVE HYDROGENATION

STATEMENT REGARDING FEDERALLY SPONSORED RESEARCH/DEVELOPMENT

This invention was made with United States government support awarded by the following agency: Department of Energy—DE-FG02-85-ER13406. The United States has certain rights in this invention.

CROSS-REFERENCE TO RELATED APPLICATIONS

Not applicable.

BACKGROUND OF THE INVENTION

The present invention relates to catalysts useful to reduce/hydrogenate ketones, aldehydes and imines. More specifically, it relates to improved ligand iron metal bifunctional catalysts for that purpose.

In connection with a variety of organic syntheses it is desirable to hydrogenate particular functional groups. Particularly desirable reactions are those which are efficient, selective insofar as hydrogenating only those groups of interest, produce few by-products that complicate purification, and use only relatively inexpensive materials.

Hydrogenation reactions often involve use of a chemical such as sodium borohydride or lithium aluminum hydride. However, these are very powerful reducing agents, making them not particularly selective.

A variety of enzymatic "hydrogenase" catalysts have been developed that facilitate hydrogenation reactions of various types. See generally J. Peters et al., X-ray Crystal Structure Of The Fe-Only Hydrogenase (Cp1) From Clostridium pasteurian To 1.8 Angstrom Resolution, 282 1853 et seq. (1998); Y. Nicolet et al., Desulfovibrio Desulfuricans Iron Hydrogenase: The Structure Shows Unusual Coordination To An Active Site Fe Binuclear Center, 7 Structure 13-23 (1999); H.-J. Fan et al., A Capable Bridging Ligand For Fe-Only Hydrogenase: Density Functional Calculations Of A Low-Energy Route For Electrolytic Cleavage And Formation Of Dihydrogen, 123 J. Am. Chem. Soc. 3828-3829 (2001). However, enzymatic catalysts often cause a variety of purification and other concerns, and often require a narrow range of reaction conditions which may not be optimal for other reasons during a synthesis.

There have been attempts to try Ru or Rh based bifunctional catalysts for the hydrogenation of polar multiple bonds. See R. Noyori et al., Asymmetric Catalysis By Architectural And Functional Molecular Engineering: Practical Chemo- And Stereoselective Hydrogenation Of Ketones, 40 Angew. Chem. Int. Ed. 40-73 (2001); T. Ikariya et al., Bifunctional Transition Melta-Based Molecular Catalysts For Asymmetric Syntheses, 4 Org. Biomol. Chem. 393-406 (2006); Y. Shvo et al., A New Group Of Ruthenium Complexes: Structure And Catalysis, 108 J. Am. Chem. Soc. 7400-7402 (1986); C. Casey et al., Hydrogen Transfer To Carbonyls And Imines From A Hydroxycyclopentadienyl Ruthenium Hydride: Evidence For Concerted Hydride And Proton Transfer, 123 J. Am. Chem. Soc. 1090-1100 (2001).

See also J. Casey et al., Isomerization And Deuterium Scrambling Evidence For A Change In the Rate-Limiting Step During Imine Hydrogenation By Shvo's Hydroxycyclopentadienyl Ruthenium Hydride, 127 J. Am. Chem. Soc. 1883-1894 (2005); J. Casey et al., Reduction Of Imines By Hydroxycyclopentadienyl Ruthenium Hydride: Intramolecular Trapping Evidence For Hydride And Proton Transfer Outside The Coordination Sphere Of The Metal, 127 J. Am. Chem. Soc. 14062-14071 (2005); J. Casey et al., Stereochemistry Of Imine Reduction By A Hydroxycyclopentadienyl Ruthenium Hydride, 128 J. Am. Chem. Soc. 2286-2293 (2006). However, Ru and Rh are relatively expensive to obtain and use.

There have also been a number of attempts to use certain iron-based catalysts in connection with certain hydrogenation reactions. Some of these catalysts selectively catalyze alkene hydrogenation. See M. Schroeder et al., Pentacarbonyliron (O) Photocatalyzed Hydrogenation And Isomerization Of Olefins, 98 J. Am. Chem. Soc. 551-558 (1976) (Fe(CO)$_5$; S. Bart et al., Preparation and Molecular and Electronic Structures of Iron(O) Dinitrogen And Silane Complexes And Their Application To Catalytic Hydrogenation And Hydrosilation, 126 J. Am. Chem. Soc. 13794-13807 (2004); E. Daida et al., Considering Fe$^{II/IV}$ Redox Processes As Mechanistically Relevant To The Catalytic Hydrogenation Of Olefins by [PhBP$^{PR}{}_3$]Fe—H$_x$ Species, 43 J. C. Inorg. Chem. 7474-7485 (2004). See also M. Radhi et al., Hydrogenation Of N-Benzylideneaniline With Molecular Hydrogen Using Iron Pentacarbonyl As Catalyst Precursor, 262 J. Organomet. Chem. 359-364 (1984). However, these publications did not report similar success in hydrogenating certain other groups such as ketones and aldehydes.

Also, there was a disclosure by Steven W. Singer, on pages 232-239 of an appendix of his PhD thesis entitled "Formation And Reactions Of A Hydroxycyclopentadienyl Ruthenium Hydride: An Organometallic Complex Containing Electronically Coupled Acidic And Hydridic Hydrogens", University Of Wisconsin (2002), regarding synthesis of a ditolyl, diphenyl, hydroxycyclopentadienyl iron hydride compound, and its use in transferring hydrogen to an aldehyde. However, the catalytic capabilities of this compound were marginal, and there were other issues of concern regarding its use.

In unrelated work, in H.-J. Knoelker et al., Demetalation Of Tricarbonyl(cyclopentadieone)iron Complexes Initiated By A Ligand Exchange Reaction With NaOH-X-Ray Analysis Of A Complex With Nearly Square-Planar Coordinated Sodium, 38 Angew. Chem. Int. Ed. 2064-2066 (1999), the authors reported on the isolation of an intermediate having the following formula, where "TMS" refers to trimethyl silyl:

However, that article did not propose a catalytic utility for this compound, much less suggest any potential hydrogenation-related function.

Thus, there is a continuing need for improved catalysts for use in hydrogenation reactions.

SUMMARY OF THE INVENTION

In one aspect the invention provides a method of reducing a ketone moiety to an alcohol moiety. One exposes the ketone moiety to a catalyst having the following formula:

where A represents hydrogen, a silyl moiety (e.g. trimethyl silyl; triphenyl silyl; triisopropyl silyl), or an alkyl moiety (e.g. tertiary butyl; methyl), B represents hydrogen, a silyl moiety (e.g. trimethyl silyl; triphenyl silyl; triisopropyl silyl), or an alkyl moiety (e.g. tertiary butyl; methyl), C linked to the five member ring represents an alkyl moiety, and D represents an alkyl moiety, where C linked to the five member ring and D both have a carbon that is part of the same cyclic moiety. For example, the C and D together could form a —$(CH_2)_4$— or —$(CH_2$—O—$CH_2)$— chain. These alkyl groups are preferably groups of less than twenty carbons, even more preferably groups of less than five carbons.

In preferred forms the catalyst has the following formula:

where the A, B, C, D, E and F which are attached to a silicon each is alkyl (e.g. methyl or isopropyl) or aryl (e.g. phenyl). These alkyl groups are preferably groups of less than twenty carbons, even more preferably groups of less than five carbons.

For example, the catalyst may have the following formula:

In further preferred forms hydrogen gas is added during the method, the reducing occurs at a temperature at or above 15° C. (e.g. most preferably at below 35° C.), at less than 5 atmosphere pressure, and the ketone moiety is a portion of a compound that has less than 30 carbons.

In another aspect the invention provides a method of reducing an aldehyde moiety to an alcohol moiety. One exposes the aldehyde moiety to a catalyst having the following formula:

where A represents hydrogen, a silyl moiety (e.g. trimethyl silyl; triphenyl silyl; triisopropyl silyl), or an alkyl moiety (e.g. tertiary butyl; methyl) B represents hydrogen, a silyl moiety (e.g. trimethyl silyl; triphenyl silyl; triisopropyl silyl), or an alkyl moiety (e.g. tertiary butyl; methyl), C linked to the five member ring represents an alkyl moiety, and D represents an alkyl moiety, where C linked to the five member ring and D both have a carbon that is part of the same cyclic moiety. For example, the C and D together could form a —$(CH_2)_4$— or —$(CH_2$—O—$CH_2)$— chain. These alkyl groups are preferably groups of less than twenty carbons, even more preferably groups of less than five carbons.

In preferred forms the catalyst has the following formula:

where the A, B, C, D, E and F which are attached to a silicon each is alkyl (e.g. methyl or isopropyl) or aryl (e.g. phenyl). These alkyl groups are preferably groups of less than twenty carbons, even more preferably groups of less than five carbons.

For example, the catalyst may have the following formula:

Again, in further preferred forms hydrogen gas is added during the method, the reducing occurs at a temperature at or above 15° C. (preferably below 35° C.), at less than 5 atmosphere pressure, and the aldehyde moiety is a portion of a compound that has less than 30 carbons.

In another aspect the invention provides a method of reducing an imine moiety to an amine moiety. One exposes the imine moiety to a catalyst having the following formula:

where A represents hydrogen, a silyl moiety (e.g. trimethyl silyl; triphenyl silyl; triisopropyl silyl), or an alkyl moiety (e.g. tertiary butyl; methyl), B represents hydrogen, a silyl moiety (e.g. trimethyl silyl; triphenyl silyl; triisopropyl silyl), or an alkyl moiety (e.g. tertiary butyl; methyl), C linked to the five member ring represents an alkyl moiety, and D represents an alkyl moiety, where C linked to the five member ring and D both have a carbon that is part of the same cyclic moiety. For example, the C and D together could form a —(CH$_2$)$_4$— or —(CH$_2$—O—CH$_2$)— chain. These alkyl groups are preferably groups of less than twenty carbons, even more preferably groups of less than five carbons.

In preferred forms the catalyst has the following formula:

where the A, B, C, D, E and F which are attached to a silicon each is alkyl (e.g. methyl or isopropyl) or aryl (e.g. phenyl). These alkyl groups are preferably groups of less than twenty carbons, even more preferably groups of less than five carbons.

For example, the catalyst may have the following formula:

In further preferred forms hydrogen gas is added during the method, the reducing occurs at a temperature at or above 15° C. (preferably below 85° C.), at less than 5 atmosphere pressure, and the aldehyde moiety is a portion of a compound that has less than 30 carbons.

The desired hydrogenation can occur with minimal reduction of alkyne and alkene bonds, and without affecting ester or ether moieties. It is also an advantageous attribute of our methods that many reactions using these catalysts can be conducted at or about room temperature with only slightly elevated hydrogen pressures. These relatively mild conditions help avoid other undesirable consequences.

Very high yields of many compounds have been obtained within less than 24 hours of reaction time.

The above and still other advantages of the present invention will be apparent from the description that follows. It should be appreciated that the following description is merely of the preferred embodiments of our invention. The claims should therefore be looked to in order to understand the full claimed scope of the invention.

DESCRIPTION OF THE PREFERRED EMBODIMENTS

Our methods involve the use of ligand iron catalysts for selective hydrogenation of ketones, aldehydes, and imines. A synthesis for the most preferred catalyst:

is described in H.-J. Knoelker et al., Demetalation Of Tricarbonyl(cyclopentadieone)iron Complexes Initiated By A Ligand Exchange Reaction With NaOH-X-Ray Analysis Of A Complex With Nearly Square-Planar Coordinated Sodium, 38 Angew. Chem. Int. Ed. 2064-2066 (1999).

More generally, we believe that compounds having the following formula:

can be created by analogous syntheses.

As general background we describe below how to make another iron hydride catalyst. We mixed a dialkyne (42 mmol), Fe(CO)$_5$ (11.04 mL, 84 mmol), and glyme (10 mL) in a Fisher-Porter glass tube. We then flushed with 3 atm of CO several times, and then disconnect the tube to the CO gas cylinder.

The closed system was then heated in a 120° C. oil bath for 22 h. After cooling, the reaction mixture was then concentrated in vacuo and the residue was then subjected to column chromatography (eluted with hexanes/CH$_2$Cl$_2$=1:1 first, and then with hexanes/EtOAc=1:1). The iron tricarbonyl was then isolated, typically as a yellow solid.

Then, under a nitrogen atmosphere, a degassed solution of NaOH (0.80 g, 20 mmol) in 30 mL of H$_2$O can be added to a solution of complex iron tricarbonyl (4.0 mmol) in 30 mL THF. The resulting biphasic mixture can be vigorously stirred at room temperature for 3.0 h before 85 wt. % of H$_3$PO$_4$ in H$_2$O (about 0.8 mL) is added to neutralize the reaction mixture.

The organic layer can then be transferred via cannula into a Schlenk flask under nitrogen and the aqueous layer can then be extracted with Et$_2$O several times. The combined organic layers were concentrated in vacuo, dissolved in degassed benzene, dried over Na$_2$SO$_4$, and filtered into another Schlenk flask. The resulting solution was pumped to dryness to afford an iron hydride, as a yellow powder.

Example 1

Figure 1:
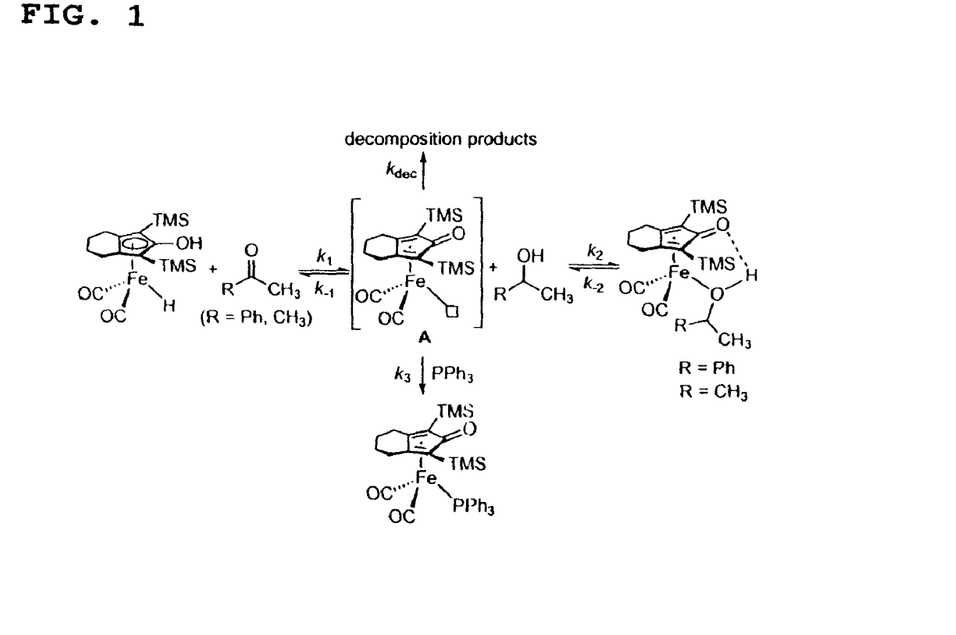
FIG. 1 depicts, in schematic form, how the most preferred catalyst of the present invention can help reduce acetophenone or acetone (representative ketones) to the corresponding alcohol.

As shown in FIG. 1, we first studied the reaction of our preferred catalyst with acetophenone in the presence of PPh$_3$ (as a trapping agent for a reactive intermediate "A"). We found a complete hydrogen transfer reaction within 4 hours under these conditions, with clean formation of the trapped iron triphenylphosphine complex and free 1-phenylethanol. Hence, this confirmed that the hydroxyl group on the catalyst could be caused to give up its hydrogen in a hydrogenation reaction.

Example 2

Figure 2:
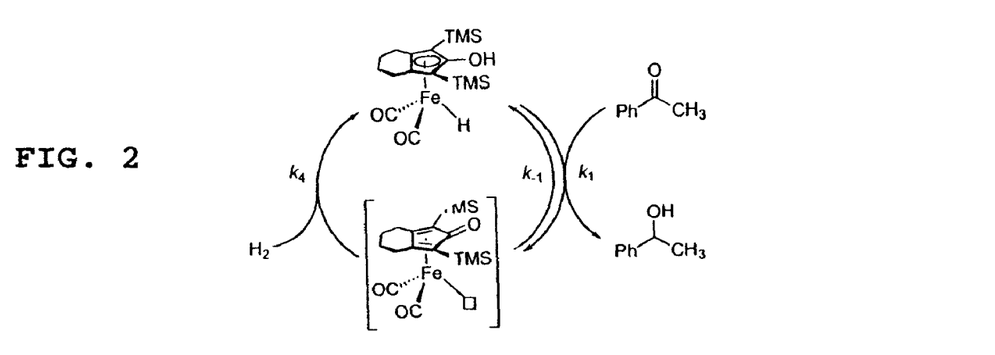
FIG. 2 schematically illustrates how, in the presence of hydrogen gas, this catalyst can be regenerated by the hydrogen so as to act as a catalyst, rather than as a consumable.
Figure 3:
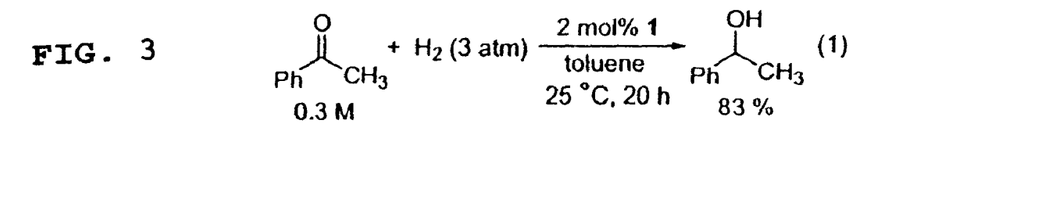
FIG. 3 illustrates a specific synthesis using hydrogen gas and acetophenone.

As shown in FIGS. 2 and 3 we then used hydrogen gas in the reaction to efficiently regenerate the catalyst (without using a trapping compound) once the hydrogen transfer had been completed. Use of the catalyst catalyzed the hydrogenation of acetophenone (or acetone) at pressures about 3 atm H$_2$, at about room temperature.

Specifically with respect to acetophenone, a resealable NMR tube containing a solution of the catalyst (11.8 mg, 30 μmol) and acetophenone (3.5 μL, 30 μmol) in preferred non-reactive solvent toluene (500 μL) was monitored by $^1$H NMR spectroscopy over days. After 12 h, about 28% of the catalyst had been converted. Extended reaction times resulted in unidentified decomposition products and free 1-phenylethanol.

A similar reaction with acetone generated the mixture of the catalyst and the expected alcohol.

Example 3

Figure 4:
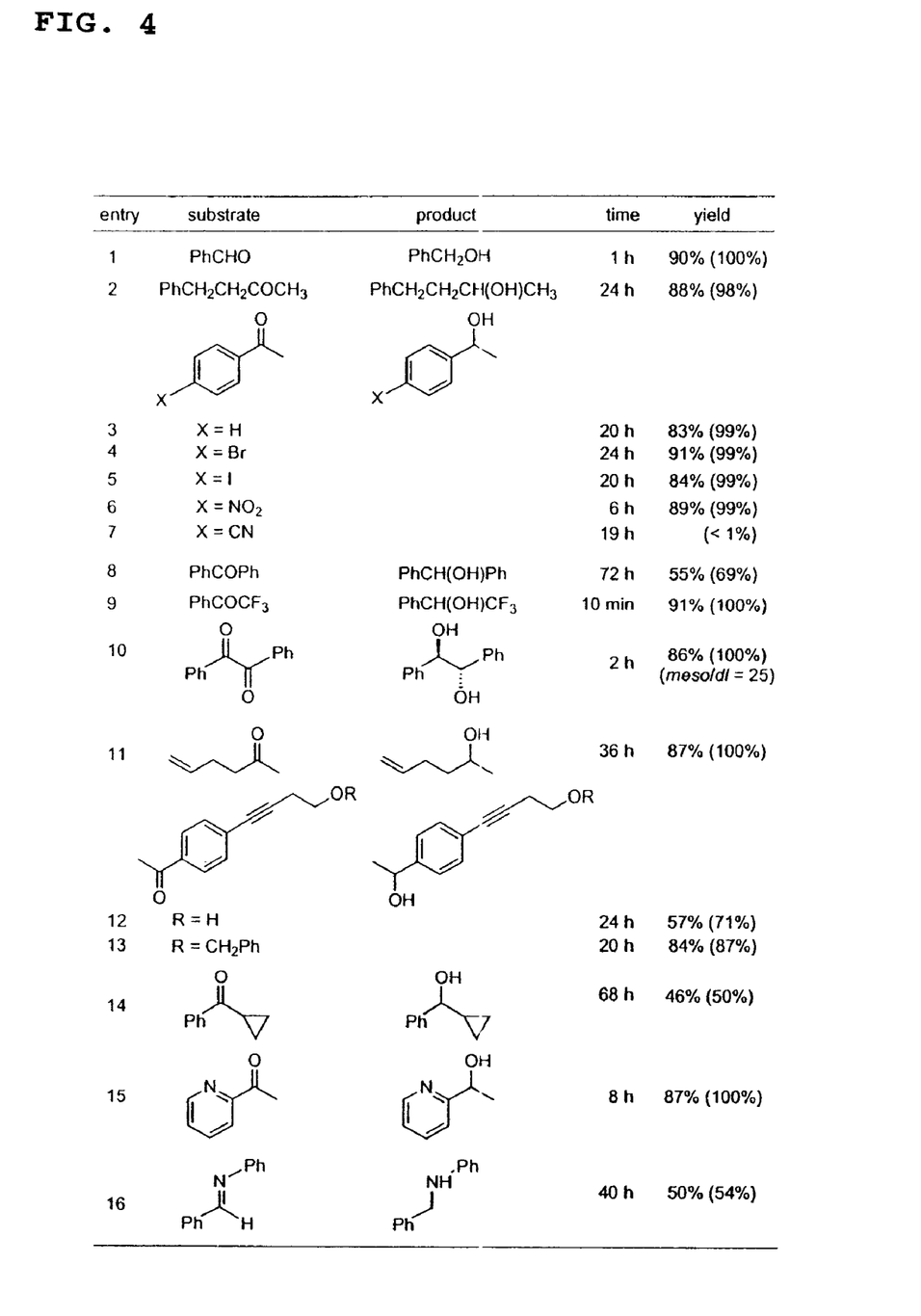
FIG. 4 is a chart listing a variety of substrates which are an aldehyde, a ketone, or an imine, which have been reduced to the corresponding alcohol or amine using hydrogen gas and a catalyst of the present invention.

As shown in FIG. 4 our preferred catalyst is an efficient and relatively selective catalyst for hydrogenation of the polar multiple bonds of aldehydes, ketones, and imines, even where those compounds contain double or triple bonded carbons. As typical reaction conditions, we used 1.5 mmol of the substrate aldehyde, ketone or imine, 30 μmol, 2.0 mol % of the catalyst, 5 mL of toluene (or alternatively diethyl ether in the case of reaction 11), and 3 atm H$_2$. We normally ran the reactions at room temperature, albeit with respect to the imine reaction we used 65° C.

In a typical experiment, a ketone substrate (1.5 mmol) was added to a Fischer-Porter bottle under a nitrogen atmosphere. The bottle was flushed several times with hydrogen gas. Then 5 mL of a solution of the catalyst in toluene (0.0060 M) was added by syringe under a flow of hydrogen and the resulting solution stirred under 3 atm of hydrogen at 25° C.

When the hydrogenation was complete, solvent was evaporated and the residue was dissolved in CDCl$_3$ and its $^1$H NMR spectrum recorded. Hydrogenation products were purified by column chromatography and their $^1$H NMR spectra matched those reported in the literature. For the hydrogenation of benzoin (entry 10, FIG. 4), the meso/d1 ratio of product was determined by examining the $^1$H NMR spectra of crude materials. The pure meso product was obtained after recrystallization from pentane. The characterization of several compounds are summarized below.

1-[4-(4-Hydroxy-1-butynyl)phenyl]ethanol (entry 12, FIG. 4) was isolated as a white solid (mp 84-85° C.).

1-[4-[4-(Phenylmethoxy)-1-butynyl]phenyl]ethanol (entry 13, FIG. 4) was isolated as a light yellow oil.

High diastereoselectivity (meso/d1=25) was seen in the hydrogenation of benzoin. High chemoselectivity was also observed: epoxides, esters, and isolated alkenes and alkynes were not hydrogenated. For ketones with isolated C=C or C≡C, only the ketone is hydrogenated (entries 11, 12, 13).

1-[4-(4-hydroxy-1-butynyl)phenyl]ethanone (entry 12, FIG. 4), 1-[4-[4-(phenylmethoxy)-1-butynyl]phenyl]ethanone (entry 13, FIG. 4), and N-benzylideneaniline (entry 16, FIG. 4) were prepared as described in the literature. See H.-J. Knoelker et al., 38 Angew. Chem. Int. Ed. 2064 (1999); G. Zhang, Synlett 619 (2005); R. Batey et al., 4 Org. Lett. 1411 (2002); and P. Andrews et al., 45 Tetrahedron Lett. 243 (2004).

Note also that carbon halogen bonds (entries 4, 5 and 9), nitro groups (entry 6), benzyl ethers (entry 13), and cyclopropyl rings (entry 14) survived the hydrogenation conditions.

A pyridine moiety can potentially bind iron and inhibit the catalytic reaction. However, 2-acetyl pyridine (entry 15) was rapidly hydrogenated. 4-acetylbenzonitrile (entry 7) was not hydrogenated, possibly due to the nitrile trapping of unsaturated intermediate A. Hydrogenation of α,β-unsaturated ketones was complicated by some reduction of the C=C double bond.

Example 4

Figure 5:
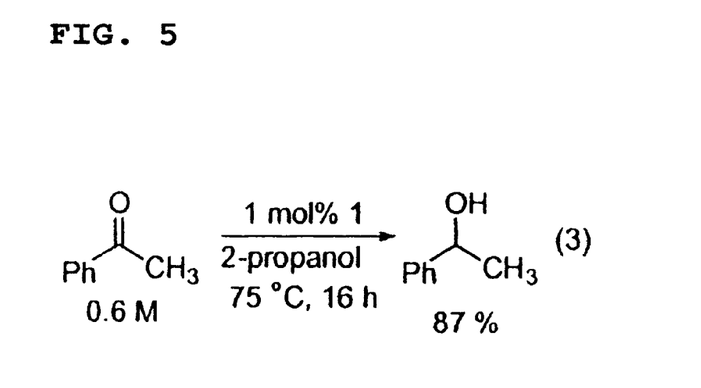
FIG. 5 schematically depicts a specific reaction involving a ketone in which instead of using hydrogen gas to regenerate the catalyst, a hydrogen donating alcohol is used for that purpose.

We next sought to confirm that hydrogen gas was not the only possible source of the hydrogen when using our catalyst. As shown in FIG. 5, we used 1 mol % of the FIG. 1 catalyst in a 0.6 mol solution of acetophenone, with 2-propanol as the hydrogen donor. This experiment was conducted at 75° C. for 16 hours, yielding 87% of the alcohol.

Under a nitrogen atmosphere, acetophenone (350 μL, 3.0 mmol) was added to a solution of 1 (11.8 mg, 30 μmol, 1 mol % catalyst) in 5 mL of 2-propanol. The resulting orange solution was stirred at 75° C. for 16 h. After cooling, the solvent was evaporated and the residue was purified by column chromatography (hexanes:ethyl acetate=4:1) to give pure 1-phenylethanol.

Example 5

Figure 6:
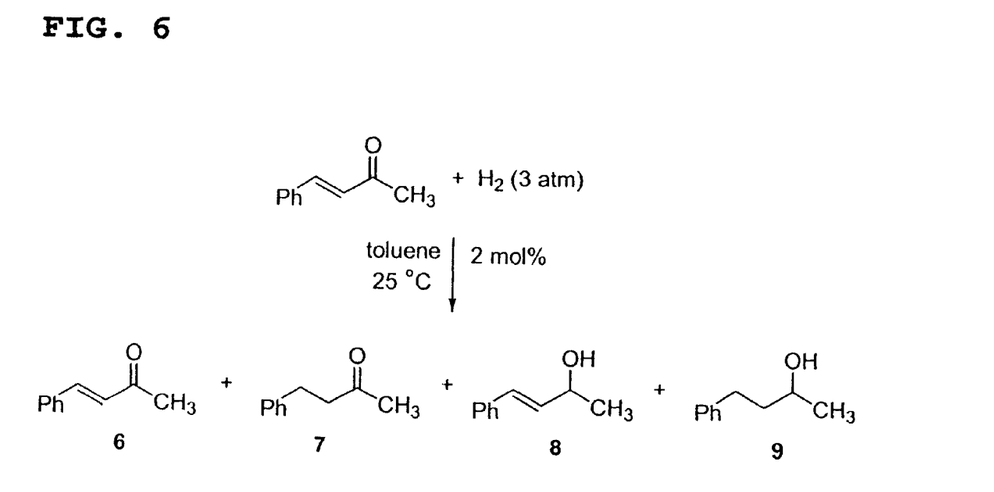
FIG. 6 depicts how under varied process conditions, differing product mixes can be obtained.

Hydrogenation of trans-4-phenyl-3-buten-2-one by the catalyst was performed with similar procedures as those for other ketones. After 1 day, an aliquot of the reaction was removed by syringe under a flow of hydrogen. Solvent was evaporated and the residue was dissolved in $CDCl_3$ and its $^1H$ NMR spectrum recorded. The reaction was monitored over 6 days. The results are summarized in FIG. 6 which illustrates that varied reaction conditions led to varied mixes of product.

Example 6

Figure 7:
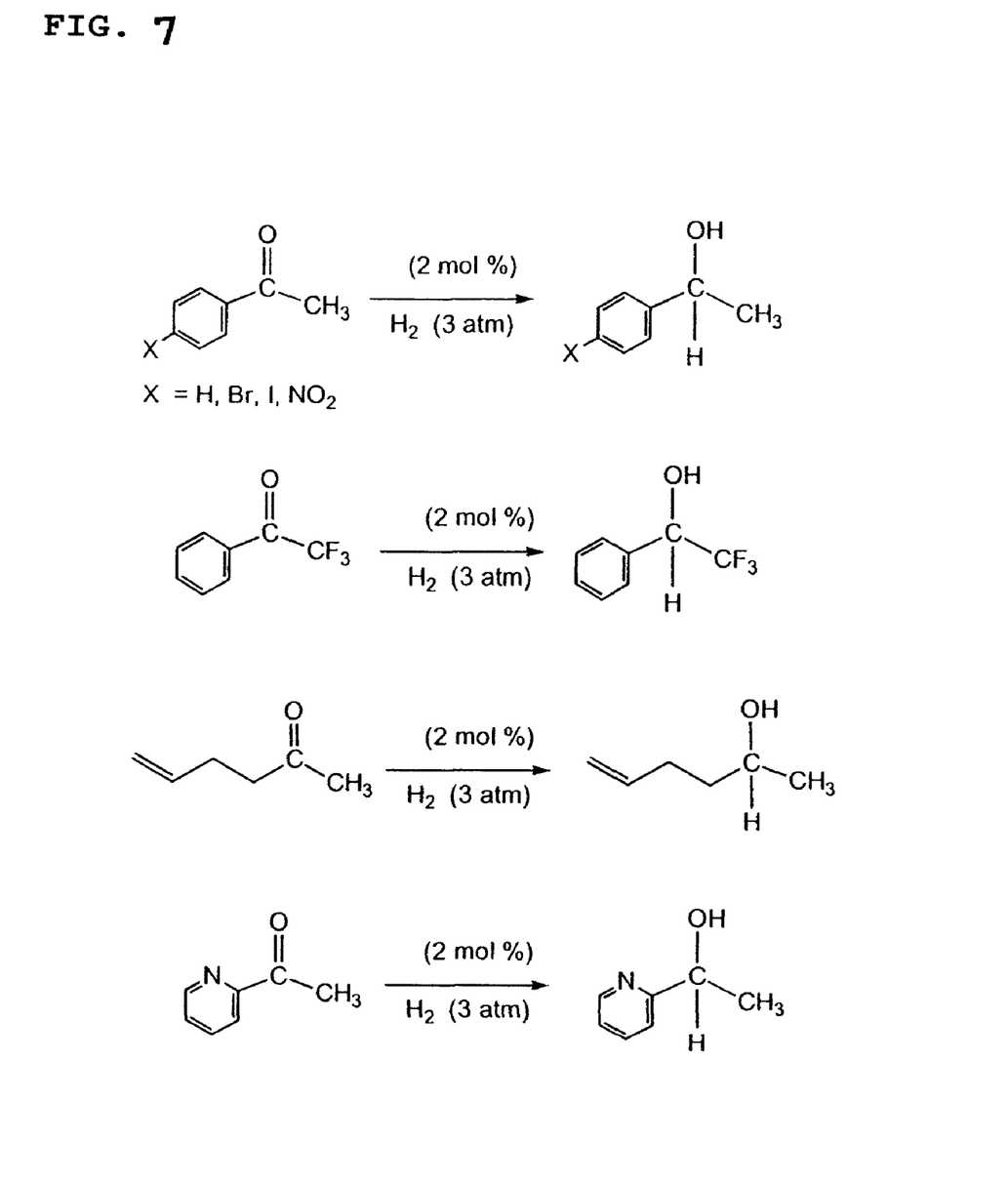
FIG. 7 illustrates several additional syntheses.

Recently, there was a published report of still other successful reductions based on our invention, in R. Bullock, An Iron Catalyst For Ketone Hydrogenations Under Mild Conditions, 2007 Angew. Chem. 03053 (9 pages) (2007). See FIG. 7 for a summary.

Other General Procedures

Generally, air-sensitive compounds were prepared and handled under a nitrogen atmosphere using standard Schlenk and inert-atmosphere box techniques. Toluene was deoxygenated and dried in a solvent purification system by passing through an activated alumina column and an oxygen scavenging column under argon. See A. Pangborn et al., 15 Organometallics 1518 (1996). Toluene was distilled from Na and benzophenone under a nitrogen atmosphere.

While a number of embodiments of the present invention have been described above, the present invention is not limited to just these disclosed examples. There are other modifications that are meant to be within the scope of the invention and claims. For example, various other catalysts which have the specified structure should be able to facilitate the hydrogenation reaction.

Hence, while the claims should be looked to in order to judge the scope of the invention, the claims are not to be limited to just the preferred embodiments.

INDUSTRIAL APPLICABILITY

The present invention provides improved methods for hydrogenating ketones, aldehydes and imines, involving using iron hydride ligands with cyclic hydroxycyclopentadienyl compounds.

We claim:

1. A method of reducing a ketone moiety to an alcohol moiety comprising exposing the ketone moiety to a catalyst having the following formula:

where A represents hydrogen, a silyl moiety, or an alkyl moiety, B represents hydrogen, a silyl moiety, or an alkyl moiety, C linked to a five member ring represents an alkyl moiety, and D represents an alkyl moiety, where C linked to the five member ring and D both have a carbon that is part of a same cyclic moiety.

2. The method of claim 1, wherein the catalyst has the following formula:

where the A, B, C, D, E and F which are attached to a silicon each is selected from the group consisting of alkyl groups and aryl groups.

3. The method of claim 1, wherein the catalyst has the following formula:

4. The method of claim 1, wherein hydrogen gas is added during the method.

5. The method of claim 1, wherein a reducing of the ketone occurs at a temperature at or above 15° C.

6. The method of claim 1, wherein the ketone moiety is a portion of a compound that has less than 30 carbons.

7. A method of reducing an aldehyde moiety to an alcohol moiety comprising exposing the aldehyde moiety to a catalyst having the following formula:

where A represents hydrogen, a silyl moiety, or an alkyl moiety, B represents hydrogen, a silyl moiety, or an alkyl moiety, C linked to a five member ring represents an alkyl moiety, and D represents an alkyl moiety, where C linked to the five member ring and D both have a carbon that is part of a same cyclic moiety.

8. The method of claim 7, wherein the catalyst has the following formula:

where the A, B, C, D, E and F which are attached to a silicon each is selected from the group consisting of alkyl groups and aryl groups.

9. The method of claim 7, wherein the catalyst has the following formula:

10. The method of claim 7, wherein hydrogen gas is added during the method.

11. The method of claim 7, wherein a reducing of the aldehyde occurs at a temperature at or above 15° C.

12. The method of claim 7, wherein the aldehyde moiety is a portion of a compound that has less than 30 carbons.

13. A method of reducing a imine moiety to an amine moiety comprising exposing the imine moiety to a catalyst having the following formula:

where A represents hydrogen, a silyl moiety, or an alkyl moiety, B represents hydrogen, a silyl moiety, or an alkyl moiety, C linked to a five member ring represents an alkyl moiety, and D represents an alkyl moiety, where C linked to the five member ring and D both have a carbon that is part of a same cyclic moiety.

14. The method of claim 13, wherein the catalyst has the following formula:

where the A, B, C, D, E and F which are attached to a silicon each is selected from the group consisting of alkyl groups and aryl groups.

15. The method of claim 13, wherein the catalyst has the following formula:

16. The method of claim 13, wherein hydrogen gas is added during the method.

17. The method of claim 13, wherein a reducing of the imine occurs at a temperature at or above 15° C.

18. The method of claim 13, wherein the imine moiety is a portion of a compound that has less than 30 carbons.

* * * * *